United States Patent [19]

Zimmerman

[11] Patent Number: 4,579,630

[45] Date of Patent: Apr. 1, 1986

[54] METHOD OF SEPARATING PRIMARY AMINES FROM TERTIARY AMINES BY AZEOTROPIC DISTILLATION

[75] Inventor: Robert L. Zimmerman, Austin, Tex.

[73] Assignee: Texaco Inc., White Plains, N.Y.

[21] Appl. No.: 699,296

[22] Filed: Feb. 7, 1985

[51] Int. Cl.$^4$ .................. B01D 3/36; C07D 265/32
[52] U.S. Cl. .................. 203/59; 203/63; 544/106; 544/177; 564/479; 564/497
[58] Field of Search ............ 203/59, 38, 63; 544/106, 177; 564/479, 497, 508

[56] References Cited

U.S. PATENT DOCUMENTS

| | | | |
|---|---|---|---|
| 2,126,600 | 8/1938 | Andrews et al. | 203/59 |
| 2,651,606 | 9/1953 | Deahl et al. | 203/59 |
| 3,331,756 | 7/1967 | Currier et al. | 203/69 |
| 3,400,129 | 9/1968 | Cour et al. | 203/52 |
| 3,420,828 | 1/1969 | Muhlbauer | 544/177 |
| 3,433,788 | 3/1969 | Somekh et al. | 203/59 |
| 4,399,307 | 8/1983 | Shioyama | 203/59 |
| 4,482,433 | 11/1984 | Drake | 203/59 |

Primary Examiner—Wilbur Bascomb
Attorney, Agent, or Firm—Jack H. Park; Kenneth R. Priem; Richard A. Morgan

[57] ABSTRACT

A method for the separation of primary amines such as bis-(2-aminoethyl)ether from tertiary amines such as N-(2-methoxyethyl)morpholine which have close boiling points via azeotropic distillation using an entrainer such as monoethanolamine is described. The N-(2-methoxyethyl) morpholine is selectively removed by the monoethanolamine. Surprisingly, a number of structurally similar compounds, such as ethylenediamine, methylethanolamine, water, ethylene glycol and isopropanolamine were discovered to be unsuitable azeotropic distillation agents either because they did not form azeotropes or for other reasons.

9 Claims, No Drawings

METHOD OF SEPARATING PRIMARY AMINES FROM TERTIARY AMINES BY AZEOTROPIC DISTILLATION

BACKGROUND OF THE INVENTION

1. Field of the Invention

The invention relates to amine extractive separation methods and more particularly relates to methods for the separation of primary amines from tertiary amines which have close boiling points, by means of azeotropic distillation.

2. Description of Other Relevant Methods in the Field

Bis-(2-aminoethyl)ether (BAEE) and N-(2-methoxyethyl)morpholine (MEM) are co-products in the production of morpholine when diethylene glycol and ammonia are used as the reactor feed. These two co-products are very difficult to separate by conventional distillation because of their close boiling points. It would be advantageous to separate these two compounds because BAEE can be methylated to form β-(N,N-dimethylaminoethyl)ether which is useful as catalyst in polyurethane isocyanate reactions according to U.S. Pat. No. 3,330,782, incorporated by reference herein.

No good method has been found for the separation of these two compounds. However, amines have been separated from other compounds according to some of the following techniques.

For example, U.S. Pat. No. 3,033,864 discloses the purification of pyrazines and piperazines by azeotropic distillation. In that patent, the goal was to remove unreacted alkanolamines by using co-distillation agents comprising aliphatic hydrocarbons, aromatic hydrocarbons and nuclear chlorinated aromatic hydrocarbons having normal boiling points between about 130° C. and 200° C. Representative examples given were octane and higher aliphatic hydrocarbons, petroleum fraction mixtures, ethyl cyclohexane, ethylbenzene, the xylenes, diethylbenzene, ethyl toluene, cumene and chlorobenzene.

A process for recovering piperazine from a mixture with triethylenediamine is described in U.S. Pat. No. 3,105,019. The inventors therein found that aliphatic hydrocarbons and especially saturated aliphatic hydrocarbons would be suitable azeotropic agents for the piperazine-triethylenediamine split if the boiling points were in the range from 110° C. to about 200° C., with particularly good results being obtained if the boiling point is within the range from about 140° C. to about 160° C. Specific compounds mentioned and tried were 3-methylheptane, 2-ethyl hexene, 1,2-dimethyl cyclohexane, meta-xylene, nonane, styrene, mesitylene, kerosene and 1-methyl naphthalene.

A method of recovering the major by-products from piperazine reaction residue is presented in U.S. Pat. No. 3,331,756. It was taught therein that hydrocarbons immiscible with diethylenetriamine and boiling within the range of about 175° C. to about 250° C. would be suitable entrainers for use in the separation of diethylenetriamine and aminoethylpiperazine. Two azeotropic agents mentioned were tetrapropylene and n-dodecane, with tetrapropylene being preferred because it gave a cleaner separation.

U.S.S.R. Pat. No. 472,122 teaches that diethylenetriamine and aminoethylpiperazine may be separated from reaction mixtures (especially those from the synthesis of a diamine and piperazine) by means of azeotropic rectification using a hydrocarbon mixture boiling at 160° C. to 174° C. yielding an azeotrope with DETA. The inventors found that the fractionation is simpler with n-decane than with dodecane or tetrapropylene.

The separation of an alkylene open chain polyamine from a piperazine compound may be accomplished by complexing the polyamine with a salt selected from the group consisting of sulfates and chlorides of copper, nickel, cobalt and zinc, according to the invention disclosed in U.S. Pat. No. 3,038,904. The complex compounds are extracted with substances such as chloroform or are allowed to precipitate out. U.S. Pat. No. 3,400,129 reveals that 2-methyl triethylenediamine can be purified in a process which incorporates a two-solvent extraction step. One of the solvents is water and the other is an organic solvent for pyrazines, such as hexene, octene, nonene, benzene, toluene, xylenes, ethyl benzene, propyl benzene, n-hexane, n-heptane, isooctane, n-nonane, methylnonane, chlorobenzene, chlorotoluenes, diethylether, furan and alkylbenzonitriles. The method includes an azeotropic distillation step where 2-methylpiperazine is distilled and a step where the purified 2-methyl triethylenediamine is recovered.

Other, less desirable methods for separating amines have been devised. For example, U.S. Pat. No. 3,420,828 to Muhlbauer uses ethylene oxide to react with BAEE to permit MEM to be distilled. U.S. Pat. No. 3,417,141 to Feldman, et al. teaches the separation of monoamines from diamines having six or more carbon atoms via liquid-liquid extraction with a polar solvent and a non-polar solvent. U.S. Pat. No. 3,038,904 to Godfrey reveals the separation of polyamines from piperazine compounds via application of metal sulfates or metal chlorides.

Further, U.S. Pat. No. 2,691,624 to Challis discloses a process for separating di-n-propylamine and tri-n-propylamine from a mixture containing di-n-propylamine, tri-n-propylamine, n-propanol and water by co-distilling with cyclohexane or benzene. The secondary amine content of an impure tertiary amine may be reduced by forming two organic phases based on the tertiary amine using hydrogen fluoride according to British Pat. No. 1,020,513 to Stevens, et al. Additionally, U.S.S.R. Pat. No. 472,122, as abstracted by Derwent, teaches the separation of diethylenetriamine and aminoethylpiperazine by azeotropic fractionation with hydrocarbons boiling at 160°-174° C. The separation of water soluble amines, such as morpholine, from their aqueous solutions may be accomplished by inert organic solvents miscible with the morpholine but not the water as taught by French Pat. No. 1,407,305. Further, Japanese Patent Document No. 55-127349 suggests simultaneous removal of water and picoline from primary arylamines by subjecting the mixture to distillation in the presence of toluene, according to the Derwent abstract.

Further, in Advances in Chemistry No. 116: Azeotropic Data III, 1973, L. H. Horsley lists a number of binary azeotropic systems.

Non-polar hydrocarbons such as methane, butane, isopentane, etc. are used in the separation of primary amines and tertiary amines according to U.S. patent application Ser. No. 581,465. These same non-polar hydrocarbons together with water are used in the extraction of the same close boiling amines, primary and tertiary, disclosed in U.S. patent application Ser. No.

581,464. Both of these applications were filed on Feb. 17, 1984.

SUMMARY OF THE INVENTION

The invention relates to a method for the separation of a primary amine from a tertiary amine, both amines having close boiling points, by azeotropically distilling a mixture containing both compounds with a selective entrainer to remove the tertiary amine with the entrainer.

The separated primary amine is used to make compounds, e.g. polyurethane catalyst. The unseparated primary amine-tertiary amine mixture has no such use.

DETAILED DESCRIPTION OF THE PREFERRED EMBODIMENTS

The method of this invention is expected to be effective for any separation of a tertiary amine from a primary amine where the amines have close boiling points. For purposes of this discussion, the amines have close boiling points if the materials boil within about 5° C. of each other. Of course, if the boiling points are not very close, the amines may be separated by the simpler process of conventional distillation.

The addition of monoethanolamine (MEA) helps to entrain the tertiary amine. As will be shown, other compounds with structures similar to MEA, such as ethylenediamine, ethylene glycol, methyl ethanolamine, isopropanol amine and water, were ineffective entrainers for this purpose. The tertiary amine has all of the nitrogen valences occupied and is, therefore, relatively non-polar as compared with the primary amine which has only one substituent on the nitrogen atom. Two amines which fulfill the requirements set out above are bis-(2-aminoethyl)ether and N-(2-methoxyethyl)morpholine.

Bis-(2-aminoethyl)ether (BAEE) and N-(2-methoxyethyl)morpholine (MEM) are both by-products in the production of morpholine from diethylene glycol and ammonia. This method of producing morpholine is referred to in U.S. Pat. Nos. 2,412,209 and 3,151,112, incorporated by reference herein. However, BAEE and MEM are difficult to separate from each other by conventional distillation because they have close boiling points.

The method of this invention allows for separating these two co-products so that both may be productively used. The method involves azeotropic distillation of the mixed co-product stream with monoethanolamine which selectively removes MEM from the mixture. Once the BAEE and the MEM have been separated, BAEE may be methylated and used most economically as polyurethane catalyst. The MEM may be recovered from the monoethanolamine by reaction and separation, but the present economic disposition of the entire stream is to burn it. At the present time, any value the BAEE-MEM mixture may have resides in the separated BAEE.

The monoethanolamine should be employed in excess quantities. Economic considerations for this novel extraction process will set an upper limit on the amount of entrainer which should be used. The azeotrope occurs at about 2:1 @ 1 atm. and excess entrainer makes for an easier separation. When the pressure is reduced to 50 mm Hg, entrainer in an amount down to about 1:1 produces good results. The best results attained in the laboratory @ 1 atm. were entrainer:tertiary amines weight ratios of 2:1 to 5:1. Generally, the monoethanolamine:tertiary amine weight proportion should be from 1:1 to 10:1, preferably 2:1 to 5:1, with processing considerations, plant design and economics setting the exact ratio.

Monoethanolamine is as stated the very most preferred entrainer for economic considerations. From purely technical considerations, an aminoalcohol boiling between 170° C. and 200° C. @ 1 atm. will do. Of these, preferable choices are 3-amino-1-propanol boiling at 184°–186° C. @ 1 atm. and 2-amino-1-propanol boiling at 173°–176° C. @ 1 atm. Criticality is demonstrated with isopropanolamine boiling at 159.9° C. @ 1 atm., for example, which entrains tertiary amine only when used in economically unsuitable excess.

The invention will be further illustrated by the following Examples.

EXAMPLE 1

Comparative Example

Distillation of Amine C-12

| | Conditions: | | Column 36″ × 1″ Goodloe packed | |
|---|---|---|---|---|
| | Reflux ratio: | | 20/2 | |
| | Charge: | | 2137 grams Amine C-12[1] | |
| Fraction | Head Temp., °C., 1 atm. | % of Charge | Composition, Area % by GC | BAEE Distribution, % |
|---|---|---|---|---|
| 1 | 96–161 | 12.4 | 86 morpholine<br>10 water | — |
| 2 | 161–185 | 26.6 | 19 methoxyethylmorpholine<br>74 bis(aminoethyl)ether | 35.4 |
| 3 | 185 | 11.7 | 5 methoxyethylmorpholine<br>95 bis(aminoethyl)ether | 19.9 |
| 4 | 185 | 21.9 | 99.9 bis(aminoethyl)ether | 39.3 |
| Residue | — | 26.6 | 11.4 bis(aminoethyl)ether<br>33.0 aminoethylmorpholine<br>55.6 2-(2-aminoethoxy)ethanol | 5.4 |

| [1]Composition of Amine C-12 by GC | Area % |
|---|---|
| Morpholine | 10.4 |
| Methoxyethylmorpholine | 13.9 |
| bis(Aminoethyl)ether | 53.8 |
| Aminoethylmorpholine | 7.3 |
| 2-(2-aminoethoxy)ethanol | 12.4 |

INVENTIVE EXAMPLE 2

| Fraction | Conditions:<br>Reflux ratio:<br>Charge:<br>Head<br>Temp.,<br>°C., 1 atm. | Column 18" × 1" Goodloe packed<br>20/5<br>500 g Amine C-12 used in Example 1 plus<br>500 g monoethanolamine<br>% of Composition,<br>Charge Area % by GC | | BAEE Distribution, % |
|---|---|---|---|---|
| 1 | 98–172 | 43 | 11.9 morpholine<br>9.9 methoxyethylmorpholine<br>0.3 unknown<br>78.0 monoethanolamine | — |
| 2 | 172–180 | 18.3 | 18 bis(aminoethyl)ether<br>91.3 monoethanolamine | 6.3 |
| 3 | 180–188 | 23.0 | 3.1 monoethanolamine<br>96.6 bis(aminoethyl)ether<br>0.3 aminoethylmorpholine | 86.1 |
| Residue | — | 13.3 | 26.20 aminoethylmorpholine<br>14.9 bis(aminoethyl)ether<br>57.8 2-(2-aminoethoxy)ethanol | 7.7 |

In Example 2 it can be seen that fraction 3 is free of methoxyethylmorpholine, thus demonstrating that the method of this invention can be used to separate a primary amine, bis(aminoethyl)ether from a tertiary amine, methoxyethylmorpholine. Using the method of this invention, more BAEE free of MEM was recovered. In Example 2 a column half as long and a reflux ratio of 20:5 instead of 20:2 was used, as compared with Example 1. Thus, Example 2 was a somewhat less efficient distillation.

EXAMPLE 3

Distillation of Amine C-12 and Monoethanolamine

| Fraction | Conditions:<br>Reflux ratio:<br>Charge:<br>Head<br>Temp.,<br>°C., 1 atm. | Column 36" × 1" Goodloe packed<br>20/2<br>1100 g Amine C-12; 500 g monoethanolamine<br>% of Composition,<br>Charge Area % by GC | | BAEE Distribution, % |
|---|---|---|---|---|
| 1 | 98–170 | 32.3 | 22.7 morpholine<br>18.2 methoxyethylmorpholine<br>50.7 monoethanolamine<br>0.3 unknown | — |
| 2 | 170–184 | 15.1 | 0.4 methoxyethylmorpholine<br>99.4 monoethanolamine<br>0.2 bis(aminoethyl)ether | 0.1 |
| 3 | 184–185 | 3.4 | 77.0 bis(aminoethyl)ether<br>23.0 monoethanolamine | 7.3 |
| 4 | 185–187 | 31.6 | 99+% bis(aminoethyl)ether | 87.7 |
| 5 | 187–202 | 6.3 | 28.2 bis(aminoethyl)ether<br>71.8 aminoethylmorpholine | 4.9 |
| Residue | — | 10.9 | 13.1 bis(aminoethyl)ether<br>86.4 2-(2-aminoethoxy)ethanol | 5.4 |

In Example 3 the same column and reflux ratio as in Example 1 was used. By adding the monoethanolamine, 87.7% of the available bis(aminoethyl)ether was recovered in 99+% purity. This compares to Example 1 where only 39.3% was recovered in 99% purity. If fractions 3 and 4 of Example 3 are combined, 95% of the available bis(aminoethyl)ether is recovered. The purity is 97.7% with 2.3% monoethanolamine being the impurity. No methoxyethylmorpholine is present in either fraction.

EXAMPLE 4

Other compounds that were tried but did not work were ethylenediamine, methylethanolamine, water, ethylene glycol and isopropanolamine. The first three did not form an azeotrope. Thus, the amount of pure bis-(aminoethyl)ether recovered was about the same as when no azeotroping agent was used. Ethylene glycol interfered with the isolation of pure bis(aminoethyl)ether because the ethylene glycol was found in all fractions. Isopropanolamine did form an azeotrope with methoxyethylmorpholine, but the methoxyethylmorpholine concentration was low, about 3% and thus its use as an entrainer is impractical.

In Examples 4A–F, 500 g of Amine C-12 and 500 g of the entrainer being tested were charged to a distillation pot. The mixture was then distilled using a 36"×1" Goodloe packed column and a reflux ratio of 10:5, 20:2 or 20:5.

EXAMPLE 4-A

Isopropanolamine, Reflux Ratio 20:5

| | Grams | Temp.<br>°C., 1 atm. | Composition, % |
|---|---|---|---|
| Cut #1 | 64.7 | 97–155 | 68.7 morpholine<br>0.9 methoxyethylmorpholine<br>30.4 isopropanolamine |
| Cut #2 | 476.5 | 155–163 | 2.4 morpholine<br>4.3 methoxyethylmorpholine<br>93.6 isopropanolamine |
| Cut #3 | 92.4 | 163–184 | 12.0 methoxyethylmorpholine<br>41.1 bis(aminoethyl)ether<br>46.9 isopropanolamine |
| Cut #4 | 257 | 184–189 | 3.2 methoxyethylmorpholine |

| | Grams | Temp. °C., 1 atm. | Composition, % |
|---|---|---|---|
| | | | 90.8 bis(aminoethyl)ether |
| | | | 5.4 aminoethylmorpholine |
| | | | 1.6 isopropanolamine |
| Bottoms | 98.5 | — | 26.9 aminoethylmorpholine |
| | | | 73.1 2-(2-aminoethoxy)ethanol |

EXAMPLE 4-B

Ethylene Glycol Monobutyl Ether, Reflux Ratio 20:2

| | Grams | Temp. °C., 1 atm. | Composition, % |
|---|---|---|---|
| Cut #1 | 111.6 | 90–168 | 58.2 morpholine |
| | | | 41.8 ethylene glycol monobutyl ether |
| Cut #2 | 350.0 | 168–170 | 100.0 ethylene glycol monobutyl ether |
| Cut #3 | 62.7 | 170–182 | 8.3 bis(aminoethyl)ether |
| | | | 10.1 methoxyethylmorpholine |
| | | | 81.7 ethylene glycol monobutyl ether |
| Cut #4 | 253.6 | 182–185 | 63.0 bis(aminoethyl)ether |
| | | | 14.1 methoxyethylmorpholine |
| | | | 22.0 ethylene glycol monobutyl ether |
| Bottoms | 214.6 | | 46.5 bis(aminoethyl)ether |
| | | | 19.3 aminoethylmorpholine |
| | | | 34.2 2-(2-aminoethoxy)ethanol |

EXAMPLE 4-C

Water, Reflux Ratio 20:5

| | Grams | Temp. °C., 1 atm. | Composition, % |
|---|---|---|---|
| Cut #1 | 486.6 | 100–101 | 100.0 water |
| Cut #2 | 96.9 | 101–184 | 57.8 morpholine |
| | | | 5.3 methoxyethylmorpholine |
| | | | 26.9 bis(aminoethyl)ether |
| Cut #3 | 140.3 | 184–187 | 13.5 methoxyethylmorpholine |
| | | | 86.5 bis(aminoethyl)ether |
| Bottoms | 262.9 | — | 2.3 methoxyethylmorpholine |
| | | | 55.1 bis(aminoethyl)ether |
| | | | 15.8 aminoethylmorpholine |
| | | | 26.8 2-(2-aminoethoxy)ethanol |

EXAMPLE 4-D

Toluene, Reflux Ratio 10:5

| | Grams | Temp. °C., 1 atm. | Composition, % |
|---|---|---|---|
| Cut #1 | 503.6 | 102–110 | 2.4 morpholine |
| | | | 97.6 toluene |
| Cut #2 | 84.8 | 110–182 | 49.2 morpholine |
| | | | 11.2 methoxyethylmorpholine |
| | | | 39.6 bis(aminoethyl)ether |
| Cut #3 | 200.4 | 182–186 | 0.3 morpholine |
| | | | 14.3 methoxyethylmorpholine |
| | | | 84.5 bis(aminoethyl)ether |
| | | | 0.9 aminoethylmorpholine |
| Cut #4 | 96.2 | 186–197 | 7.5 methoxyethylmorpholine |
| | | | 84.9 bis(aminoethyl)ether |
| | | | 7.6 aminoethylmorpholine |
| Bottoms | 98 | | 5.1 bis(aminoethyl)ether |
| | | | 27.6 aminoethylmorpholine |
| | | | 67.4 2-(2-aminoethoxy)ethanol |

EXAMPLE 4-E

Ethylene Glycol, Reflux Ratio 20:5

| | Grams | Temp. °C., 1 atm. | Composition, % |
|---|---|---|---|
| Cut #1 | 145.0 | 166–197 | 44.1 morpholine |
| | | | 26.2 methoxyethylmorpholine |
| | | | 3.3 bis(aminoethyl)ether |
| | | | 2.7 aminoethylmorpholine |
| | | | 23.7 ethylene glycol |
| Cut #2 | 755.4 | 197–202 | 0.9 methoxyethylmorpholine |
| | | | 32.6 bis(aminoethyl)ether |
| | | | 3.3 aminoethylmorpholine |
| | | | 63.2 ethylene glycol |
| Bottoms | 91.5 | — | 7.9 aminoethylmorpholine |
| | | | 81.8 2(2-aminoethoxy)ethanol |
| | | | 10.4 ethylene glycol |

EXAMPLE 4-F

Ethylenediamine, Reflux Ratio 20:5

| | Grams | Temp. °C., 1 atm. | Composition, % |
|---|---|---|---|
| Cut #1 | 535.0 | 117–120 | 5.7 morpholine |
| | | | 94.3 ethylenediamine |
| Cut #2 | 55.2 | 120–185 | 21.0 morpholine |
| | | | 17.9 methoxyethylmorpholine |
| | | | 53.4 bis(aminoethyl)ether |
| | | | 7.7 ethylenediamine |
| Cut #3 | 257.6 | 185–188 | 11.5 methoxyethylmorpholine |
| | | | 88.2 bis(aminoethyl)ether |
| | | | 0.3 aminoethylmorpholine |
| Cut #4 | 46.2 | 188–203 | 50.9 bis(aminoethyl)ether |
| | | | 48.0 aminoethylmorpholine |
| | | | 1.1 2-(2-aminoethoxy)ethanol |
| Bottoms | — | — | 21.2 aminoethylmorpholine |
| | | | 78.8 2-(2-aminoethoxy)ethanol |

The above examples illustrate that MEM and BAEE may be separated by the MEA extraction technique. Although only batch equipment was used in these extractions, continuous or continuous countercurrent apparatus may be used also.

Many modifications may be made in the method of this invention by one skilled in the art without departing from the spirit and scope of the inventive method which is defined only by the appended claims.

I claim:

1. A method for the separation of primary and tertiary amines having close boiling points comprising azeotropically distilling a mixture comprising a primary amine and a tertiary amine having close boiling points with an entrainer selected from the group consisting of monoethanolamine, 3-amino-1-propanol and 2-amino-1-propanol to selectively remove the tertiary amine with the entrainer from the primary amine.

2. A method for the separation of primary and tertiary amines having close boiling points comprising azeotropically distilling a mixture comprising a primary amine and a tertiary amine having close boiling points with monoethanolamine to selectively remove the tertiary amine with the monoethanolamine.

3. The method of claim 2 wherein the weight ratio of monoethanolamine:tertiary amine is 1:1 to 10:1.

4. A method for the separation of bis-(2-aminoethyl)ether from N-(2-methoxyethyl)morpholine consisting essentially of
azeotropically distilling a mixture comprising bis-(2-aminoethyl)ether and N-(2-methoxyethyl)morpholine with an entrainer selected from the group consisting of monoethanolamine, 3-amino-1-propanol and 2-amino-1-propanol to selectively remove the N-(2-methyoxyethyl)morpholine with the entrainer.

5. The method of claim 4 wherein the weight ratio of entrainer:N-(2-methoxyethyl)morpholine is 1:1 to 10:1.

6. The method of claim 4 wherein the weight ratio of entrainer:N-(2-methoxyethyl)morpholline is 2:1 to 5:1.

7. A method for the separation of bis-(2-aminoethyl)ether from N-(2-methoxyethyl)morpholine consisting essentially of
azeotropically distilling a mixture comprising bis-(2-aminoethyl)ether and N-(2-methoxyethyl)morpholine with monoethanolamine to selectively remove the N-(2-methoxyethyl)morpholine with the monoethanolamine.

8. The method of claim 7 wherein the weight ratio of monoethanolamine:N-(2-methoxyethyl)morpholine is 1:1 to 10:1.

9. The method of claim 7 wherein the weight ratio of monoethanolamine:N-(2-methoxyethyl)morpholine is 2:1 to 5:1.

* * * * *